United States Patent
Guilbot et al.

(10) Patent No.: US 11,590,066 B2
(45) Date of Patent: Feb. 28, 2023

(54) COMPOSITION OF LIPOAMINO ACIDS AND ALKANEDIOLS, PROCESS FOR THE PREPARATION THEREOF, AND COSMETIC OR PHARMACEUTICAL COMPOSITION RESULTING THEREFROM

(71) Applicant: SOCIETE D'EXPLOITATION DE PRODUITS POUR LES INDUSTRIES CHIMIQUES SEPPIC, Paris (FR)

(72) Inventors: Jérôme Guilbot, Castres (FR); Georges Dacosta, Saix (FR); Virginie Barthe, Paris (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 258 days.

(21) Appl. No.: 16/956,432

(22) PCT Filed: Dec. 12, 2018

(86) PCT No.: PCT/FR2018/053218
§ 371 (c)(1),
(2) Date: Jun. 19, 2020

(87) PCT Pub. No.: WO2019/122606
PCT Pub. Date: Jun. 27, 2019

(65) Prior Publication Data
US 2020/0323761 A1    Oct. 15, 2020

(30) Foreign Application Priority Data
Dec. 20, 2017 (FR) ...................................... 1762622

(51) Int. Cl.
A61K 8/81 (2006.01)
A61Q 19/00 (2006.01)
C07C 233/47 (2006.01)
C07C 31/20 (2006.01)

(52) U.S. Cl.
CPC .............. *A61K 8/817* (2013.01); *A61Q 19/00* (2013.01); *C07C 31/20* (2013.01); *C07C 233/47* (2013.01); *A61K 2800/10* (2013.01)

(58) Field of Classification Search
CPC .... A61K 8/817; A61K 2800/10; A61Q 19/00; C07C 31/20; C07C 233/47
USPC ....................................................... 514/772.7
See application file for complete search history.

(56) References Cited

U.S. PATENT DOCUMENTS

| 2,463,779 A | 3/1949 | Kester et al. |
| 6,703,517 B2 | 3/2004 | Hattori et al. |
| 2014/0128309 A1 | 5/2014 | Banowski et al. |

FOREIGN PATENT DOCUMENTS

| EP | 0415598 A1 * | 3/1991 | ........... A61K 8/4913 |
| FR | 2765105 A1 | 12/1998 | |
| FR | 2771632 A1 | 6/1999 | |
| WO | 92/21318 A1 | 12/1992 | |
| WO | 94/26694 A1 | 11/1994 | |
| WO | 2013/158824 A2 | 10/2013 | |

OTHER PUBLICATIONS

International Search Report, dated Feb. 19, 2019, from corresponding PCT application No. PCT/FR2018/053218.
French Search Report, dated Nov. 7, 2018, from corresponding French application No. 1762622.

* cited by examiner

*Primary Examiner* — Kristin A Vajda
(74) *Attorney, Agent, or Firm* — Nixon & Vanderhye

(57) ABSTRACT

Disclosed are a new composition of lipoamino acids and alkanediols, a process for the preparation thereof, and a cosmetic or pharmaceutical composition resulting therefrom.

20 Claims, No Drawings

COMPOSITION OF LIPOAMINO ACIDS AND ALKANEDIOLS, PROCESS FOR THE PREPARATION THEREOF, AND COSMETIC OR PHARMACEUTICAL COMPOSITION RESULTING THEREFROM

BACKGROUND OF THE INVENTION

Field of the Invention

The present invention relates to a novel method for preparing N-acyl derivatives of amino acids, of (oligo) peptides or of partial or total protein hydrolyzates, having a high degree of conversion of the starting materials used. The present invention also relates to the use of these N-acyl compounds obtained for preparing cosmetic or pharmaceutical compositions for topical use or industrial detergency compositions.

Description of the Related Art

N-Acyl amino acid derivatives, also known as lipoamino acids (LAA), are anionic surfactants which are formed by a polar head originating from a residue of at least one amino acid, or else from a residue of (oligo)peptides or else from residues of partial or total protein hydrolyzates, and by a hydrocarbon chain of lipophilic nature, originating from fatty acid chlorides or fatty acid methyl esters, which are themselves derived from oleochemistry.

These N-acyl derivatives of amino acids, of (oligo)peptides or else of partial or total protein hydrolyzates are commonly used first of all as ingredients which contribute foaming and cleansing properties for the preparation of cosmetic compositions, such as, for example, shower gels or shampoos, or else as ingredients which contribute biological properties for the preparation of cosmetic compositions intended to prevent or correct unsightly skin effects; said biological properties are, for example, anti-aging, slimming, firming, depigmenting or pro-pigmenting properties.

The N-acyl derivatives of amino acids, of (oligo)peptides or else of partial or total protein hydrolyzates are commonly synthesized by acylation of one or more amino acids in the presence of acid chloride, under experimental conditions known as Schotten-Baumann conditions.

Such a method is disclosed, for example, in the American patents U.S. Pat. Nos. 2,463,779 and 6,703,517, in the publication J. Am. Oil Chem. Soc. 78 (1956) 172, and in the international applications published under the numbers WO 92/21318 and WO 94/26694.

This acylation method comprises a preliminary stage of salification of the amino acid, followed by a stage of acylation of the amino acid salt with an acid chloride, and then acidification of the N-acyl salt obtained.

The first stage consists in neutralizing the amino acid, dissolved beforehand in water or in a mixture of water and an organic cosolvent, with an inorganic base, usually aqueous sodium hydroxide or aqueous potassium hydroxide. The carboxyl group is then in an ionized form, thus making possible better solubility of the amino acid in water. The pH of this aqueous solution lies between 9.0 and 12.0, which makes it possible to ensure that the amine functional group of the amino acid is not protonated.

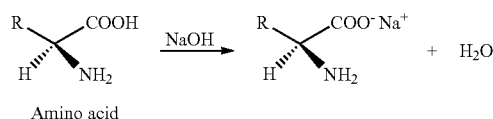

Amino acid

The second stage is the acylation stage proper. At this stage, the acid chloride is gradually added to the neutralized solution of amino acid, at ambient temperature. The nucleophilic amine functional group attacks the electrophilic carbon of the carbonyl functional group. This results in the formation of an amide bond between the two starting substrates and also in the formation of hydrochloric acid. This acid is directly neutralized in situ by gradual addition of an inorganic base (regulation of the pH in the vicinity of 10.0).

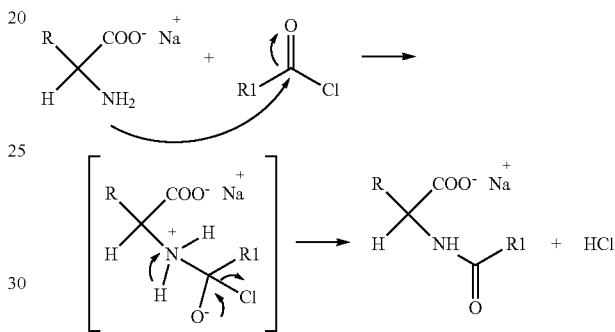

At this stage, the side reaction of hydrolysis of the acid chloride to give a soap is also possible. It must, however, be minimized so as to achieve a satisfactory conversion of the amino acid to its N-acyl derivative and to efficiently isolate them, since an excessively high content of soap (or fatty acid salt) may induce phase separation of the reaction medium and/or odor or toxicity problems (for the $C_8$ and $C'_{11}$ chains, for example).

The two main reaction parameters that enable the formation of soap to be controlled are the stirring speed during the reaction phase, optimization of which makes possible an improvement in the contact surface area of the chloride with the medium, and the optional addition, during the stage of dissolution of the amino acid, of an acylation cosolvent, such as, for example, acetone, methyl ethyl ketone, isopropanol or glycols.

This addition of cosolvent makes it possible to improve the affinity of the acid chloride for the reaction medium. In such a case, the acylation cosolvent must be astutely chosen so as to avoid or minimize the formation of new side products resulting from the reaction between this same cosolvent and the acid chloride, such as, for example, byproducts originating from esterification side reactions.

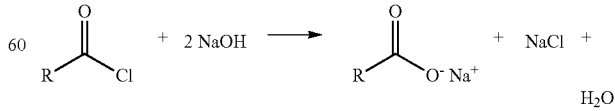

The final stage consists of a finishing stage, of giving form to the N-acyl derivative formed, and two alternatives are possible:

The first consists in adjusting the pH value of the reaction medium obtained to the vicinity of 7. The N-acyl derivative is isolated as is in solution, without any additional purification, and comprises the acylation salts, the unreacted amino acids and the optional cosolvent. It is thus in a salified form, and more precisely a carboxylate form, in aqueous solution and with a purity generally of less than 50%.

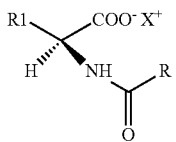

R1 = Amino acid side chain
R = Cocoyl chain
X = Counterion

The second consists in precipitating the N-acyl derivative by acidifying the reaction mixture to a pH value in the region of 2 and in then performing several filtration and washing operations, concluding with a final drying of the medium obtained. This procedure thus makes it possible to remove all the salts generated during the acylation reaction, the optional acylation cosolvent and all the unreacted amino acids. In this case, the N-acyl derivative is in a non-salified form, with a carboxylic acid functional group, and a solid form, more particularly a pulverulent form, and with a purity of greater than 80%.

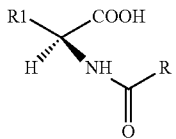

R1 = Amino acid side chain
R = Cocoyl chain
X = Counterion

The Schotten-Baumann process described above exhibits the advantage of carrying out N-acylation reactions with rapid kinetics, due to the very high reactivity of the acid chlorides toward nucleophilic compounds and functional groups (for example, the amine functional group), without a substantial supply of energy, such as, for example, heat energy, in a solvent medium predominantly formed of water, with high yields.

Nowadays, however, formulators of cosmetic products face difficulties regarding the use of powders when it comes to preparing finished products.

In addition, if byproducts originating from esterification side reactions are present in too great a quantity and if the acyl radical of the fatty acid in question contains at least 12 carbon atoms, a lower reproducibility is observed of the biological properties associated with the N-acyl amino acids formed, and more particularly associated with the composition containing said target N-acyl amino acids and the products of associated esterification side reactions. Moreover, it is commonly desirable to limit the mass content of residual fatty acids to less than or equal to 15% and more particularly to the lowest value possible.

For that reason there is a need to develop a method for the direct synthesis of highly pure liquid salts of salified N-acyl amino acids without precipitation/filtration/drying stages.

SUMMARY OF THE INVENTION

The inventors found that it was possible to achieve this result using acylation cosolvents that can also be used as final dilution solvents, it being understood that such cosolvents must also make it possible to control and/or minimize the formation of fatty acids during the acylation stage, be poorly reactive to acid chlorides under the reaction conditions, allow for the effective elimination of the salts generated during acylation by simple liquid/liquid decantation at high temperature, and lastly make it possible to obtain a solution of homogeneous N-acyl amino acids with neutral pH.

The French patent application published under the publication number FR 2765105A2 describes a method for preparing a mixture of N-acyl amino acid derivatives using, in particular, an undefined quantity of propylene glycol (or 1,2-propanediol), lauroyl chloride, and indicates a residual lauric acid content in the final product of 15% by mass.

That is why, according to a first aspect, a subject of the invention is a composition ($C_1$) comprising, per 100% of its mass:

(a)—a mass proportion of greater than or equal to 50% by mass and less than or equal to 95% by mass, more particularly greater than or equal to 60% by mass and less than or equal to 80% by mass, of a compound of formula (I) or of a mixture of compounds of formula (I):

$$X\text{—}[CH_2]_p\text{—}C(\text{=}O)\text{—}Y\text{—}OH \quad (I),$$

in which p represents an integer greater than or equal to 10 and less than or equal to 20, Y represents either a divalent radical of formula ($II_a$):

$$\text{—}[N(R_3)\text{—}CH(R_2)\text{—}C(\text{=}O)\text{—}]_m\text{—} \quad (II_a),$$

in which $R_3$ represents a hydrogen atom or a methyl radical, m represents an integer greater than or equal to 1 and less than or equal to 4 and $R_2$ represents a hydrogen atom or a radical chosen from methyl, isopropyl, isobutyl, 1-methylpropyl, benzyl and 3-aminopropyl radicals; or a divalent radical of formula ($II_b$):

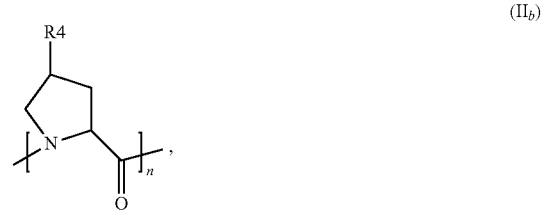

in which $R_4$ represents a hydrogen atom or a hydroxyl radical and n represents an integer greater than or equal to 1 and less than or equal to 4; and X represents either a methyl radical or a monovalent radical of formula (III):

$$HO\text{—}Y'\text{—}C(\text{=}O)\text{—} \quad (III),$$

in which Y' represents either the divalent radical of formula ($II_a$) as defined previously, or the divalent radical of formula ($II_b$) as defined previously, it being understood that when X represents the radical of formula (III), Y and Y' are identical;

(b)—a mass proportion of greater than 0% by mass and less than or equal to 25% by mass, more particularly greater than or equal to 5% by mass and less than or equal to 15% by mass, of a linear or branched alkanediol containing from six to eight carbon atoms;

(c)—a mass proportion of greater than or equal to 0% by mass and less than or equal to 5% by mass, more particularly greater than or equal to 0.5% by mass and less than or equal to 2.5% by mass, of a compound of formula (V) or of a mixture of compounds of formula (V):

$$X-[CH_2]_p-C(=O)-OH \quad (V),$$ 

in which X represents a methyl radical, p represents an integer greater than or equal to 10 and less than or equal to 20, or a mixture of said compounds of formula (V); and (d)—a mass proportion of greater than 0% by mass and less than 50% by mass, more particularly greater than or equal to 10% by mass and less than or equal to 25% by mass, of water, it being understood that the pH of said composition is less than or equal to 3, more particularly less than or equal to 2.0.

According to a particular aspect, a subject of the invention is the composition ($C_1$) as defined previously, characterized in that, in formulae (I) and (V), X represents a methyl radical; according to this particular aspect, the composition ($C_1$) as defined previously is most particularly characterized in that in formula (I), the divalent radical Y represents the divalent radical of formula (HA:

$$-[NH-CH(R_2)-C(=O)-]_m- \quad (II_{a1}),$$ 

in which m represents an integer greater than or equal to one and less than or equal to four and $R_2$ represents a hydrogen atom or a radical chosen from methyl, isopropyl, isobutyl, 1-methylpropyl, benzyl or 3-aminopropyl radicals.

According to another particular aspect, the composition ($C_1$) as defined above is characterized in that in formula (I), the divalent radical Y represents the divalent radical of formula ($II'_{a1}$):

$$-NH-CH_2-C(=O)- \quad (II'_{a1}),$$ 

According to another particular aspect, the composition ($C_1$) as defined above is characterized in that in formula (I), the divalent radical Y represents the divalent radical of formula ($II'_{a2}$):

$$-NH-CH[-CH(CH_3)-CH_2-CH_3]-C(=O)- \quad (II'_{a2}).$$ 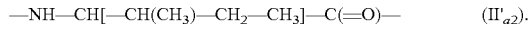

According to another particular aspect, the composition ($C_1$) as defined above is characterized in that in formulae (I) and (V), the monovalent radical $X-(CH_2)_p-C(=O)-$ represents the palmitoyl radical.

The term "alkanediol containing from six to eight carbon atoms" notably denotes, in the composition ($C_1$) as defined previously, 1,6-hexanediol, 1,2-hexanediol, 2-methyl-2,4-pentanediol or 1,2-octanediol.

A subject of the invention is also a method for preparing the composition ($C_1$) as defined previously, characterized in that it comprises the following successive steps:

a step a) during which said alkanediol containing from six to eight carbon atoms is mixed with water to form a mixture ($S_1$) containing, per 100% of its mass, from 5% by mass to 70% by mass, and more particularly from 5% by mass to 30% by mass, of said alkanediol and from 30% by mass to 95% by mass, and more particularly from 70% by mass to 95% by mass, of water;

a step b) during which a compound of formula ($VI_a$):

or of formula (IVb):

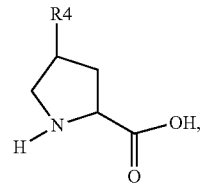

or a mixture of at least one compound of formula ($VI_a$) or ($VI_b$) with at least one other compound of formula ($VI_a$) or ($VI_b$) is added to said mixture ($S_1$) in a proportion such that the mixture ($M_1$) obtained contains, per 100% of its mass, from 5% by mass to 50% by mass, more particularly from 5% by mass to 30% by mass, of said compound of formula ($VI_a$) or ($VI_b$) or of said mixture of compounds of formula ($VI_a$) and/or ($VI_b$) and from 50% by mass to 95% by mass, more particularly from 50% by mass to 70% by mass, of said mixture ($S_1$);

a step c) during which sodium hydroxide or potassium hydroxide is added to said mixture ($M_1$) to form a mixture ($M_2$) having a pH greater than or equal to 9, more particularly greater than or equal to 9.5;

a step d) during which between 0.7 and 1.0 molar equivalent, more particularly between 0.8 and 0.9 molar equivalent, of an acid chloride of formula (VII):

$$X-[CH_2]_p-C(=O)-Cl \quad (VII),$$ 

in which X and p are as defined in formula (I) above, or a mixture of acid chlorides of formula (VII), is poured into said mixture ($M_2$), while maintaining the pH at a value greater than or equal to 9, more particularly greater than or equal to 9.5, by the joint addition of sodium hydroxide or potassium hydroxide, said step e) resulting in the formation of a mixture ($M_3$);

a step e) during which said mixture ($M_3$) is acidified until a pH of less than or equal to 3, more particularly less than or equal to 2.5, is reached;

a step f) of decantation for the purpose of drawing off the mother liquors;

if necessary or if desired, at least one step g) of washing with brined water to obtain, after decantation, said desired composition.

Step a) of the method as defined above is generally performed at ambient temperature. According to a particular aspect thereof, said alkanediol containing from six to eight carbon atoms is mixed with water to form a mixture ($S_1$) containing, per 100% of its mass, from 10% by mass to 20% by mass of said alkanediol and from 80% by mass to 90% by mass of water.

Step b) of the method as defined above is generally performed at ambient temperature. According to a particular aspect thereof, said compound of formula ($VI_a$) or of formula ($VI_b$), or said mixture of at least one compound of formula ($VI_a$) or ($VI_b$) with at least one other compound of formula ($VI_a$) or ($VI_b$), is added to said mixture ($S_1$) in a proportion such that the mixture ($M_1$) obtained contains, per 100% of its mass, from 10% by mass to 25% by mass of said compound of formula ($VI_a$) or ($VI_b$) or of said mixture of compounds of formula ($VI_a$) and/or ($VI_b$) and from 75% by mass to 90% by mass of said mixture ($S_1$).

Step d) of the method as defined above is generally performed by gradually pouring the acid chloride of formula (VII) or the mixture of acid chlorides of formula (VII) into said mixture ($M_2$) while maintaining the reaction temperature in an interval of between 10° C. and 40° C.; then by leaving the reaction to proceed for approximately thirty minutes at a temperature of between 40° C. and 60° C.

Step f) of the method as defined above is generally performed by maintaining the reaction temperature in an interval of between 40° C. and 60° C.

A subject of the invention is also a method for preparing a cosmetic, dermocosmetic, dermopharmaceutical or pharmaceutical composition for topical use (C) comprising a mass proportion of greater than or equal to 5% by mass and less than or equal to 30% by mass of a compound of formula (I') or of a mixture of compounds of formula (I'):

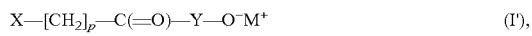

in which p represents an integer greater than or equal to 10 and less than or equal to 20, $M^+$ represents a sodium cation, Y represents either a divalent radical of formula ($II_a$):

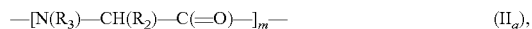

in which $R_3$ represents a hydrogen atom or a methyl radical, m represents an integer greater than or equal to 1 and less than or equal to 4 and $R_2$ represents a hydrogen atom or a radical chosen from methyl, isopropyl, isobutyl, 1-methylpropyl, benzyl and 3-aminopropyl radicals; or a divalent radical of formula ($II_b$):

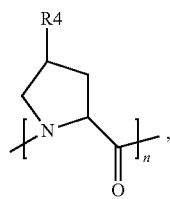

in which $R_4$ represents a hydrogen atom or a hydroxyl radical and n represents an integer greater than or equal to 1 and less than or equal to 4; and X represents either a methyl radical or a monovalent radical of formula (III):

in which Y' represents either the divalent radical of formula ($II_a$) as defined previously, or the divalent radical of formula ($II_b$) as defined previously, it being understood that when X represents the radical of formula (III), Y and Y' are identical;

(b)—a mass proportion of greater than 5% by mass and less than or equal to 30% by mass of a linear or branched alkanediol containing from six to eight carbon atoms;

(d)—a mass proportion of greater than 40% by mass and less than 90% by mass of water, it being understood that the pH of said composition (C) is less than or equal to 9 and greater than or equal to 5.5, said method being characterized in that it includes a step h), during which the necessary quantities of linear or branched alkanediol containing from six to eight carbon atoms, of aqueous sodium hydroxide solution and of water are added simultaneously or sequentially to the composition ($C_1$) as defined in any one of claims 1 to 7 to obtain the proportions and pH value as defined above.

The expression "for topical use" used in the definition of said cosmetic, dermocosmetic, dermopharmaceutical or pharmaceutical composition for topical use (C) obtained by the method as defined above means that said composition is employed by application to the skin, the hair, the scalp or the mucous membranes, whether it is a direct application in the case of a cosmetic, dermocosmetic, dermopharmaceutical or pharmaceutical composition or an indirect application, for example in the case of a body hygiene product in the form of a textile or paper wipe, or sanitary products intended to be in contact with the skin or the mucous membranes.

The cosmetic, dermocosmetic, dermopharmaceutical or pharmaceutical composition for topical use (C) obtained by the method as defined above can be packaged in pressurized form in an aerosol device or in a device of "pump-action spray" type, in a device equipped with a perforated wall, for example a grill, or in a device equipped with a ball applicator (known as a "roll-on"). When it is packaged in small bottles, said composition (C) can be applied in the form of fine droplets by means of mechanical pressurization devices or propellant gas devices. The propellants which can be combined with the composition (C) according to the invention include hydrofluorinated compounds, such as dichlorodifluoromethane, trichlorofluoromethane, difluoroethane, isobutane, butane and propane.

Said composition (C) obtained by the method as defined above may also contain excipients and/or active principles commonly used in the field of formulations for topical use, in particular cosmetic, dermocosmetic, pharmaceutical or dermopharmaceutical formulations.

Such excipients are, for example, foaming and/or detergent surfactants, thickening and/or gelling surfactants, thickeners and/or gelling agents, stabilizers, film-forming compounds, solvents and cosolvents, hydrotropic agents, plasticizers, opacifiers, nacreous agents, sequestrants, chelating agents, antioxidants, fragrances, essential oils, preserving agents, conditioning agents, particles which provide a visual effect or which are intended for encapsulating active agents, exfoliating particles, texturing agents, optical brighteners.

Such active principles are, for example, intended to provide a treating and/or protective action to the skin or the hair, such as sunscreens, mineral fillers or pigments, insect repellents, deodorants or bleaching agents intended for bleaching bodily hair and the skin.

Among the water-soluble antioxidants that may be included in said composition (C) are, for example, ascorbic acid, glutathione, tartaric acid, oxalic acid and tetrasodium glutamate diacetate.

Among the water-soluble sequestrants that may be included in said composition (C) are, for example, ethylenediaminetetraacetic acid (EDTA) salts, for instance the sodium salt of EDTA, diethylenetriaminepentaacetic acid (DTPA) salts, for instance the sodium salts of DTPA, and acetyl glutamic acid (Dissolvine range).

Among the water-soluble dyes that may be included in said composition (C) are, for example, caramel, Yellow 5, Acid Blue 9/Blue 1, Green 5, Green 3/Fast Green FCF 3, Orange 4, Red 4/Food Red 1, Yellow 6, Acid Red 33/Food Red 12, Red 40, cochineal carmine (Cl 15850, Cl 75470), Ext. Violet 2, Red 6-7, Ferric Ferrocyanide, Ultramarines, Acid Yellow 3/Yellow 10, Acid Blue 3 and Yellow 10.

Among the color-stabilizing water-soluble agents that may be included in said composition (C) are, for example, tris(tetramethylhydroxypiperidinol) citrate, sodium benzotriazolyl butylphenol sulfonate or benzotriazolyl dodecyl p-cresol.

As examples of foaming and/or detergent surfactants optionally present in said composition (C), mention may be made of topically acceptable anionic, cationic, amphoteric or nonionic foaming and/or detergent surfactants commonly used in this field of activity.

Among the foaming and/or detergent anionic surfactants that may be included in said composition (C) are, for example, alkali metal salts, alkaline-earth metal salts, ammonium salts, amine salts, amino alcohol salts of alkyl ether sulfates, of alkyl sulfates, of alkylamido ether sulfates, of alkylarylpolyether sulfates, of monoglyceride sulfates, of alpha-olefin sulfonates, of paraffin sulfonates, of alkyl phosphates, of alkyl ether phosphates, of alkyl sulfonates, of alkylamide sulfonates, of alkylaryl sulfonates, of alkyl carboxylates, of alkylsulfosuccinates, of alkyl ether sulfosuccinates, of alkylamide sulfosuccinates, of alkyl sulfoacetates, of alkyl sarcosinates, of acylisethionates, of N-acyl taurates, of acyl lactylates, of N-acyl amino acid derivatives, of N-acyl peptide derivatives, of N-acyl protein derivatives and of fatty acids.

Among the foaming and/or detergent amphoteric surfactants optionally present in said composition (C), mention may be made of alkylbetaines, alkylamidobetaines, sultaines, alkylamidoalkylsulfobetaines, imidazoline derivatives, phosphobetaines, amphopolyacetates and amphopropionates.

Among the foaming and/or detergent cationic surfactants optionally present in said composition (C), mention may be made particularly of quaternary ammonium derivatives.

Among the foaming and/or detergent nonionic surfactants optionally present in said composition (C), mention may be made more particularly of alkylpolyglycosides containing a linear or branched, saturated or unsaturated aliphatic radical and containing from eight to twelve carbon atoms; castor oil derivatives, polysorbates, coconut kernel amides and N-alkylamines.

As examples of texturing agents optionally present in said composition (C), mention may be made of N-acyl amino acid derivatives, for example lauroyl lysine sold under the name AMINOHOPE™LL, octenyl starch succinate sold under the name DRYFLO™, myristyl polyglucoside sold under the name MONTANOV 14, cellulose fibers, cotton fibers, chitosan fibers, talc, sericite, mica and perlite.

Examples of active principles optionally present in said composition (C) include:

vitamins and derivatives thereof, for example retinol (vitamin A) and esters thereof (for example retinyl palmitate), ascorbic acid (vitamin C) in salt form and esters thereof, sugar derivatives of ascorbic acid (for example ascorbyl glucoside), tocopherol (vitamin E) and esters thereof (for example tocopheryl acetate), vitamin B3 or B10 (niacinamide and derivatives thereof);—compounds having a lightening or depigmenting action on the skin, for example SEPIWHITE™ MSH, arbutin, kojic acid, hydroquinone, VEGEWHITE™, GATULINE™, SYNERLIGHT™, BIOWHITE™, PHYTOLIGHT™, DERMALIGHT™, CLARISKIN™, MELASLOW™, DERMAWHITE™, ETHIOLINE, MELAREST™, GIGAWHITE™, ALBATINE™ and LUMISKIN™;

compounds with calmative action, such as SEPICALM™ S, allantoin and bisabolol;

anti-inflammatory agents;

compounds showing a moisturizing action, for example diglycerol, triglycerol, urea, hydroxyureas, glyceryl glucoside, diglyceryl glucoside, polyglyceryl glucosides, erythrityl glucoside, sorbityl glucoside, xylityl glucoside, the composition sold under the brand name AQUAXYL™ comprising xylityl glucoside, anhydroxylitol and xylitol;

compounds showing a slimming or lipolytic action, such as caffeine or derivatives thereof, ADIPOSLIM™ and ADIPOLESS™;

plant extracts rich in tannins, polyphenols and/or isoflavones, for example grape extracts, pine extracts, wine extracts, olive extracts; soybean extracts, for example Raffermine™; wheat extracts, for example TENSINE™ or GLIADINE™; terpene-rich plant extracts; freshwater or seawater algal extracts; marine extracts in general such as corals;

compounds with antimicrobial action or with purifying action, for example LIPACIDE™ C8G, LIPACIDE™ UG, SEPICONTROL™ A5; OCTOPIROX™ or SENSIVA™ SC50;

compounds with an energizing or stimulating property, such as Physiogenyl™ panthenol and derivatives thereof such as SEPICAP™ MP;

antiaging active agents such as SEPILIFT™ DPHP, LIPACIDE™ PVB, SEPIVINOL™, SEPIVITAL™, MANOLIVA™, PHYTO-AGE™, TIMECODE™; SURVICODE™;

anti-photoaging active agents;

active agents for increasing the synthesis of extracellular matrix components, for example collagen, elastins and glycosaminoglycans;

active agents acting favorably on chemical cellular communication, such as cytokines, or on physical cellular communication, such as integrins;

active agents which create a "heating" sensation on the skin, such as skin capillary circulation activators (for example nicotinic acid derivatives) or products which create a "freshness" sensation on the skin (for example menthol and derivatives thereof);

active agents which improve the skin capillary circulation, for example venotonic agents;

draining active agents; decongesting active agents, for example extracts of *Ginkgo biloba*, ivy, common horse chestnut, bamboo, ruscus, butcher's-broom, *Centella asiatica*, fucus, rosemary or willow;

active agents acting as skin-tautening agents, for example plant protein hydrolyzates, hydrolyzates of marine origin, for instance hydrolyzates of *laminaria* extracts, fish cartilage hydrolyzates, marine elastin, the product sold by the company SEPPIC under the brand name SESAFLASH™, and collagen solutions.

skin tanning or browning agents, for example dihydroxyacetone, isatin, alloxan, ninhydrin, glyceraldehyde, mesotartaric aldehyde, glutaraldehyde and erythrulose.

As examples of deodorants optionally present in said composition (C), mention may be made of alkali metal silicates, zinc salts, such as zinc sulfate, zinc gluconate, zinc chloride or zinc lactate; quaternary ammonium salts, such as cetyltrimethylammonium salts or cetylpyridinium salts; glycerol derivatives, such as glyceryl caprate, glyceryl caprylate or polyglyceryl caprate; 1,2-decanediol, 1,3-propanediol, salicylic acid, sodium bicarbonate, cyclodextrins, metal zeolites, Triclosan™, aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, or complexes of aluminum chlorohydrate and of glycol, such as the aluminum chlorohydrate and propylene glycol complex, the aluminum dichlorohydrate and propylene glycol complex, the aluminum sesquichlorohydrate and propylene glycol complex, the aluminum chlorohydrate and polyethylene glycol complex, the aluminum dichlorohydrate and polyethylene glycol complex or the aluminum sesquichlorohydrate and polyethylene glycol complex.

As examples of thickeners or gelling agents optionally present in said composition (C), mention may be made of linear or branched or crosslinked polymers of polyelectrolyte type, such as the partially or totally salified acrylic acid homopolymer, the partially or totally salified methacrylic acid homopolymer, the partially or totally salified 2-methyl-[(1-oxo-2-propenyl)amino]-1-propanesulfonic acid (AMPS) homopolymer, copolymers of acrylic acid and of AMPS, copolymers of acrylamide and of AMPS, copolymers of vinylpyrrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethylacrylamide, copolymers of AMPS and of tris(hydroxymethyl)acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethylacrylamide, terpolymers of acrylic or methacrylic acid, of AMPS and of acrylamide, copolymers of acrylic acid or methacrylic acid and of alkyl acrylates, the carbon chain of which comprises between 4 and 30 carbon atoms and more particularly between 10 and 30 carbon atoms, copolymers of AMPS and of alkyl acrylates, the carbon chain of which comprises between 4 and 30 carbon atoms and more particularly between 10 and 30 carbon atoms, linear, branched or crosslinked terpolymers of at least one monomer having a free, partially salified or totally salified strong acid function, with at least one neutral monomer, and at least one monomer of formula (VIII):

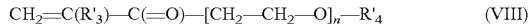

$$CH_2=C(R'_3)-C(=O)-[CH_2-CH_2-O]_n-R'_4 \quad (VIII)$$

in which $R'_3$ represents a hydrogen atom or a methyl radical, $R'_4$ represents a linear or branched alkyl radical containing from eight to thirty carbon atoms and n represents a number greater than or equal to one and less than or equal to fifty.

The linear or branched or crosslinked polymers of polyelectrolyte type that may be included in said composition (C) may be present in the form of a solution, an aqueous suspension, a water-in-oil emulsion, an oil-in-water emulsion, a powder, for example the products sold under the names SIMULE™ EG, SIMULGEL™ EPG, SEPIGEL™ 305, SIMULGEL™ 600, SIMULGEL™ NS, SIMULGEL™ INS 100, SIMULGEL™ FL, SIMULGEL™ A, SIMULGEL™ SMS 88, SEPINOV™ EMT 10, SEPIPLUS™ 400, SEPIPLUS™ 265, SEPIPLUS™ S, SEPIMAX™ ZEN, ARISTOFLEX™ AVC, ARISTOFLEX™ AVS, NOVEMER™ EC-1, NOVEMER™ EC 2, ARISTOFLEX™ HMB, COSMEDIA™ SP, FLOCARE™ ET 25, FLOCARE™ ET 75, FLOCARE™ ET 26, FLOCARE™ ET 30, FLOCARE™ ET 58, FLOCARE™ PSD 30, VISCOLAM™ AT 64 AND VISCOLAM™ AT 100; polysaccharides constituted solely of saccharides, such as glucans or glucose homopolymers, glucomannoglucans, xyloglucans, galactomannans in which the degree of substitution (DS) of the D-galactose units on the D-mannose main chain is between 0 and 1 and more particularly between 1 and 0.25, for instance galactomannans originating from *cassia* gum (DS=⅕), from locust bean gum (DS=¼), from tara gum (DS=⅓), from guar gum (DS=½) or from fenugreek gum (DS=1); polysaccharides constituted of saccharide derivatives, such as galactan sulfates and more particularly carrageenans and agar, uronans and more particularly algins, alginates and pectins, heteropolymers of saccharides and of uronic acids and more particularly xanthan gum, gellan gum, gum arabic exudates and karaya gum exudates, glucosaminoglycans; cellulose, cellulose derivatives such as methylcellulose, ethyl-cellulose, hydroxypropyl cellulose, silicates, starch, hydrophilic starch derivatives, polyurethanes.

As examples of oils that may be present in said composition (C), mention may be made of mineral oils such as liquid paraffin, liquid petroleum jelly, isoparaffins or white mineral oils; oils of animal origin such as squalene or squalane; plant oils, such as phytosqualane, sweet almond oil, coconut kernel oil, castor oil, jojoba oil, olive oil, rapeseed oil, groundnut oil, sunflower oil, wheat germ oil, corn germ oil, soybean oil, cotton oil, alfalfa oil, poppy oil, pumpkin oil, evening primrose oil, millet oil, barley oil, rye oil, safflower oil, candlenut oil, passionflower oil, hazelnut oil, palm oil, shea butter, apricot kernel oil, coriander seed oil, beechnut oil, beauty-leaf oil, sisymbrium oil, avocado oil, calendula oil, oils derived from flowers or vegetables, ethoxylated plant oils; synthetic oils, for instance fatty acid esters such as butyl myristate, propyl myristate, isopropyl myristate, cetyl myristate, isopropyl palmitate, octyl palmitate, butyl stearate, hexyldecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, fatty acid monoglycerides, diglycerides and triglycerides, for instance glyceryl triheptanoate, alkylbenzoates, hydrogenated oils, poly(alpha-olefins), polyolefins such as poly(isobutane), synthetic isoalkanes, for instance isohexadecane, isododecane, perfluorinated oils; silicone oils, for instance dimethylpolysiloxanes, methylphenylpolysiloxanes, silicones modified with amines, silicones modified with fatty acids, silicones modified with alcohols, silicones modified with fatty alcohols and fatty acids, silicones modified with polyether groups, epoxy-modified silicones, silicones modified with fluoro groups, cyclic silicones and silicones modified with alkyl groups. In the present patent application, the term "oils" refers to compounds and/or mixtures of compounds which are water-insoluble, and which have a liquid appearance at a temperature of 25° C.

As examples of waxes optionally present in said composition (C), mention may be made of beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax; silicone waxes; plant waxes; fatty alcohols and fatty acids that are solid at ambient temperature; glycerides that are solid at ambient temperature. In the present patent application, the term "waxes" refers to compounds and/or mixtures of compounds which are water-insoluble, and which have a solid appearance at a temperature of greater than or equal to 45° C.

As examples of emulsifying nonionic surfactants that may be included in said composition (C), mention may be made of fatty acid esters of sorbitol, for instance the products sold under the names MONTANE™ 40, MONTANE™ 60, MONTANE™ 70, MONTANE™ 80 and MONTANE™ 85; compositions comprising glyceryl stearate and stearic acid ethoxylated with between 5 mol and 150 mol of ethylene oxide, for instance the composition comprising stearic acid ethoxylated with 135 mol of ethylene oxide and glyceryl stearate sold under the name SIMULSOL™ 165; mannitan esters, ethoxylated mannitan esters; sucrose esters; methyl glucoside esters; alkyl polyglycosides containing a linear or branched, saturated or unsaturated aliphatic radical, containing from 14 to 36 carbon atoms, for instance tetradecyl polyglucoside, hexyldecyl polyglucoside, octadecyl polyglucoside, hexyldecyl polyxyloside, octadecyl polyxyloside, eicosyl polyglucoside, dodecosyl polyglucoside, (2-octyldodecyl) polyxyloside, (12-hydroxystearyl) polyglucoside; compositions of linear or branched, saturated or unsaturated fatty alcohols containing from 14 to 36 carbon atoms and of alkyl polyglycosides as described previously, for example the compositions sold under the brand names MONTANOV™ 68, MONTANOV™ 14, MONTANOV™ 82, MONTANOV™ 202, MONTANOV™ S, MONTANOV™ WO18, MONTANOV™ L, FLUIDANOV™ 20X and EASYNOV™.

As examples of agents for protecting against ultraviolet radiation from the sun optionally present in said composition (C), pigments, organic sunscreens and inorganic sunscreens are denoted.

As pigments used as an agent for protecting against ultraviolet radiation from the sun optionally present in said composition (C), there are for example titanium dioxide, brown iron oxides, yellow iron oxides, black iron oxides or red iron oxides, or else white or colored nacreous pigments such as titanium mica.

As organic sunscreens used as an agent for protecting against ultraviolet radiation from the sun optionally present in said composition (C), there are for example:
  those of the family of benzoic acid derivatives, such as para-aminobenzoic acids (PABAs), notably monoglyceryl esters of PABA, ethyl esters of N,N-propoxy PABA, ethyl esters of N,N-diethoxy PABA, ethyl esters of N,N-dimethyl PABA, methyl esters of N,N-dimethyl PABA, butyl esters of N,N-dimethyl PABA;
  those of the family of anthranilic acid derivatives, such as homomenthyl-N-acetyl anthranilate;
  those of the family of salicylic acid derivatives, such as amyl salicylate, homomenthyl salicylate, ethylhexyl salicylate, phenyl salicylate, benzyl salicylate, p-isopropanolphenyl salicylate;
  those of the family of cinnamic acid derivatives, such as ethylhexyl cinnamate, ethyl-4-isopropyl cinnamate, methyl-2,5-diisopropyl cinnamate, p-methoxypropyl cinnamate, p-methoxyisopropyl cinnamate, p-methoxyisoamyl cinnamate, p-methoxyoctyl cinnamate (p-methoxy 2-ethylhexyl cinnamate), p-methoxy 2-ethoxyethyl cinnamate, p-methoxycyclohexyl cinnamate, ethyl-α-cyano-β-phenyl cinnamate, 2-ethylhexyl-α-cyano-β-phenyl cinnamate, glyceryl di-para-methoxy mono-2-ethylhexanoyl cinnamate;
  those of the family of benzophenone derivatives, such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxy benzophenone-5-sulfonate, 4-phenylbenzophenone, 2-ethylhexyl-4'-phenyl benzophenone-2-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, benzalkonium methosulfate camphor; urocanic acid, ethyl urocanate;
  those of the family of sulfonic acid derivatives, such as 2-phenylbenzimidazole-5-sulfonic acid and its salts; the family of triazine derivatives, such as hydroxyphenyl triazine, ethylhexyloxyhydroxyphenyl-4-methoxyphenyltriazine, 2,4,6-trianilino-(p-carbo-2'-ethylhexyl-1'-oxy)-1,3,5-triazine, the 4,4-((6-(((1,1-dimethylethyl)amino)carbonyl)phenyl)amino)-1,3,5-triazine-2,4-diyl diimino) bis(2-ethylhexyl) ester of benzoic acid, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl) benzotriazole; dibenzazine; dianisoylmethane, 4-methoxy-4"-t-butylbenzoylmethane; 5-(3,3-dimethyl-2-norbornylidene)-3-pentan-2-one; 2-(4-diethylamino-2-hydroxybenzoyl)benzoic acid hexyl ester, 2,4-bis{[4-(2-ethylhexyloxy)-2-hydroxy]phenyl}-6-(4-methoxyphenyl)-1,3,5-triazine, 2,4,6-tris[4-(2-ethylhexyloxycarbonyl)anilino]-1,3,5-triazine, 2-ethylhexyl dimethoxybenzylidene dioxoimidazolidine propionate, the family of diphenylacrylate derivatives, such as 2-ethylhexyl-2-cyano-3,3-diphenyl-2-propenoate or ethyl-2-cyano-3,3-diphenyl-2-propenoate;
  those of the family of polysiloxanes, such as benzylidene siloxane malonate.

As inorganic sunscreens used as an agent for protecting against ultraviolet radiation from the sun optionally present in said composition (C), there are for example titanium oxides, zinc oxides, cerium oxide, zirconium oxide, yellow, red or black iron oxides, chromium oxides. These mineral sunblocks may or may not be micronized, may or may not have undergone surface treatments and may optionally be present in the form of aqueous or oily predispersions.

The examples that follow illustrate the invention without, however, limiting it.

DESCRIPTION OF THE PREFERRED EMBODIMENTS

Preparation of Compositions ($C_1$) According to the Invention

The common procedure is as follows:
  Introduction, at ambient temperature and with mechanical stirring, of 20% by mass of isoleucine into 80% by mass of a mixture of water/diol (80/20 by mass),
  Addition of 30% sodium hydroxide to achieve a pH of approx. 11.5,
  Gradual flow of palmitoyl chloride (0.8 molar equivalent), while maintaining the pH at approximately 11-12 with 30% sodium hydroxide, at a temperature of 20 to 40° C.,
  Breaking up with 37% hydrochloric acid q.s. to achieve a pH of approx. 2,
  Drawing off of mother liquors at 60° C.,
  Washing with 5% brined water,
  Decantation and drawing off at 60° C.

The features of compositions ($C_1$) are collated in table 1 below:

TABLE 1

|  | ($C_{1A}$) | ($C_{1B}$) | ($C_{1C}$) |
|---|---|---|---|
| Diol ($IV_a$) or ($IV_b$) | Hexylene glycol | 1,2-Hexanediol | 1,6-Hexanediol |
| Diol content | 10.2% by mass | 20.1% by mass | 3.9% by mass |
| Palmitoic acid content (V) | 2.1% by mass | 2.0% by mass | 1.3% by mass |
| Water content | 11.8% by mass | 6.3% by mass | 7.1% by mass |
| N-Palmitoyl isoleucine content (I) | 75.9% by mass | 71.6% by mass | 87.7% by mass |
| Presence of byproducts | No | No | No |
| pH 1% | 2.7 | 2.3 | 2.5 |
|  | ($C_{1D}$) | | |
| Diol ($IV_a$) or ($IV_b$) | 1,2-Octanediol | | |
| Diol content ($IV_a$) or ($IV_b$) | 22.4% by mass | | |
| Octanoic acid content (V) | 2.2% by mass | | |
| Water content | 17.6% by mass | | |
| N-Octanoyl glycine content (I) | 57.8% by mass | | |
| Presence of byproducts | No | | |
| pH of the composition | 2.1 | | |

Preparation of a Comparative Composition ($C_{21}$)

Introduction, at ambient temperature and with mechanical stirring, of 20% by mass of glycocoll (glycine) into 80% by mass of a mixture of water/diol (85/15 by mass), Addition of 30% sodium hydroxide to achieve a pH of approx. 10, Gradual flow of lauroyl chloride (0.9 molar equivalent), while maintaining the pH at approximately 10 with 30% sodium hydroxide, at a temperature of 18 to 36° C., Breaking up with 37% hydrochloric acid q.s. to achieve a pH of approx. 2, Drawing off of mother liquors at 60° C., Washing with 5% brined water, Decantation and drawing off at 65° C.

The features of the composition ($C_{21}$) thus obtained are collated in table 2 below.

Preparation of a Comparative Composition ($C_{22}$)

Introduction, at ambient temperature and with mechanical stirring, of 20% by mass of a mixture of glycine, L-aspartic acid, L-glutamic acid and L-alanine, in the mass proportions of glycine/L-aspartic acid/L-glutamic acid/L-alanine of 10%/35%/45%/10% per 100% by mass of said mixture of amino acids, into 80% by mass of a mixture of water/diol (85/15 by mass), Addition of 30% sodium hydroxide to achieve a pH of approx. 10, Gradual flow of lauroyl chloride (0.9 molar equivalent), while maintaining the pH at approximately 10 with 30% sodium hydroxide, at a temperature of 18 to 36° C., Breaking up with 37% hydrochloric acid q.s. to achieve a pH of approx. 2, Drawing off of mother liquors at 60° C., Washing with 5% brined water, Decantation and drawing off at 65° C.

The features of the composition ($C_{22}$) thus obtained are collated in table 2 below.

TABLE 2

|  | ($C_{21}$) | ($C_{22}$) |
|---|---|---|
| Diol ($IV_a$) or ($IV_b$) | 1,2-Propanediol | 1,2-Propanediol |
| Diol content ($IV_a$) or ($IV_b$) | 0.9% by mass | 1.9% by mass |
| Lauric acid content (V) | 4.1% by mass | 12.9% by mass |
| Water content | 11.0% by mass | 27.5% by mass |
| N-Lauroyl glycine content (I) | 83.2% by mass | 11.9% by mass |
| N-Lauroyl alanine content (I) | — | 11.0% by mass |
| N-Lauroyl aspartic acid content (I) | — | 12.2% by mass |
| N-Lauroyl glutamic acid content (I) | — | 20.4% by mass |
| Presence of byproducts | 0.8% by mass | 2.2% by mass |
| pH of the composition | pH = 2.1 | pH = 2.2 |

The analysis of the compositions ($C_{1A}$), ($C_{1B}$), ($C_{1C}$) and ($C_{1D}$), the subject of the present invention, shows that they contain no byproducts and that their fatty acid concentration is minimal, whereas the comparative compositions ($C_{21}$) and ($C_{22}$) prepared in the presence of 1,2-propanediol are characterized by a higher content of residual fatty acids and by the presence of byproducts.

The invention claimed is:

1. A composition ($C_1$) comprising, per 100% of mass:
   (a) —a mass proportion of greater than or equal to 50% by mass and less than or equal to 95% by mass of a compound of formula (I) or of a mixture of compounds of formula (I):

$$X—[CH_2]_p—C(=O)—Y—OH \qquad (I),$$
   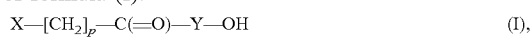

in which p represents an integer greater than or equal to 10 and less than or equal to 20, Y represents either a divalent radical of formula ($II_a$):

$$—[N(R_3)—CH(R_2)—C(=O)—]_m— \qquad (II_a),$$
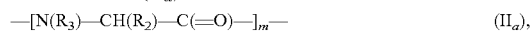

in which $R_3$ represents a hydrogen atom or a methyl radical, m represents an integer greater than or equal to 1 and less than or equal to 4 and $R_2$ represents a hydrogen atom or a radical chosen from methyl, isopropyl, isobutyl, 1-methylpropyl, benzyl and 3-aminopropyl radicals; or a divalent radical of formula ($II_b$):

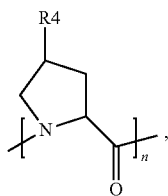

(IIb)

in which $R_4$ represents a hydrogen atom or a hydroxyl radical and n represents an integer greater than or equal to 1 and less than or equal to 4; and X represents either a methyl radical or a monovalent radical of formula (III):

HO—Y'—C(=O)— (III), in which Y' represents either the divalent radical of formula (IIa) as defined previously, or the divalent radical of formula (IIb) as defined previously, wherein when X represents the radical of formula (III), Y and Y' are identical;

(b) —a mass proportion of greater than 0% by mass and less than or equal to 25% by mass of a linear or branched alkanediol containing from six to eight carbon atoms;

(c) —a mass proportion of greater than or equal to 0% by mass and less than or equal to 5% by mass of a compound of formula (V) or of a mixture of compounds of formula (V):

X—[CH$_2$]$_p$—C(=O)—OH (V), in which X represents a methyl radical, p represents an integer greater than or equal to 10 and less than or equal to 20, or a mixture of said compounds of formula (V); and (d) —a mass proportion greater than 0% by mass and less than or equal to 50% by mass of water, it being understood that the pH of said composition is less than or equal to 3.

2. The composition ($C_1$) as defined in claim 1, wherein, in formulae (I) and (V), X represents a methyl radical.

3. The composition ($C_1$) as defined in claim 2, wherein in formula (I), the divalent radical Y represents the divalent radical of formula (II$_{a1}$):

—[NH—CH(R$_2$)—C(=O)—]$_m$— (II$_{a1}$), in which m represents an integer greater than or equal to one and less than or equal to four and $R_2$ represents a hydrogen atom or a radical chosen from methyl, isopropyl, isobutyl, 1-methylpropyl, benzyl or 3-aminopropyl radicals.

4. The composition ($C_1$) as defined in claim 3, wherein in that in formula (I), the divalent radical Y represents the divalent radical of formula (II'$_{a1}$):

—NH—CH$_2$—C(=O)— (II'$_{a1}$).

5. The composition ($C_1$) as defined in claim 3, wherein in formula (I), the divalent radical Y represents the divalent radical of formula (II'$_{a2}$):

—NH—CH[—CH(CH$_3$)—CH$_2$—CH$_3$]—C(=O)— (II'$_{a2}$).

6. The composition ($C_1$) as defined in claim 1, wherein in formulae (I) and (V), the monovalent radical X—(CH$_2$)$_p$—C (=O)— represents the palmitoyl radical.

7. The composition ($C_1$) as defined in claim 1, wherein said diol containing from six to eight carbon atoms is chosen from 1,6-hexanediol, 1,2-hexanediol, 2-methyl 2,4-pentanediol or 1,2-octanediol.

8. A method for preparing the composition ($C_1$) as defined in claim 1, comprising the following successive steps:

a step a) during which said alkanediol containing from six to eight carbon atoms is mixed with water to form a mixture ($S_1$) containing, per 100% of mass, from 5% by mass to 70% by mass of said alkanediol and from 30% by mass to 95% by mass of water;

a step b) during which a compound of formula (VI$_a$):

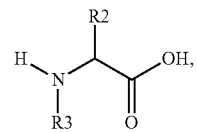

(VI$_a$)

or of formula (IV$_b$):

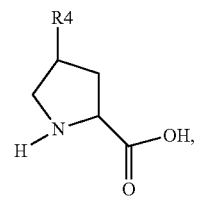

(VI$_b$)

or a mixture of at least one compound of formula (VI$_a$) or (VI$_b$) with at least one other compound of formula (VI$_a$) or (VI$_b$) is added to said mixture ($S_1$) in a proportion such that the mixture ($M_1$) obtained contains, per 100% of mass, from 5% by mass to 50% by mass of said compound of formula (VI$_a$) or (VI$_b$) or of said mixture of compounds of formula (VI$_a$) and/or (VI$_b$) and from 50% by mass to 95% by mass of said mixture ($S_1$);

a step c) during which sodium hydroxide or potassium hydroxide is added to said mixture ($M_1$) to form a mixture ($M_2$) having a pH greater than or equal to 9;

a step d) during which an acid chloride of formula (VII):

X—[CH$_2$]$_p$—C(=O)—Cl (VII), in which X and p are as defined in formula (I) above, or a mixture of acid chlorides of formula (VII), is poured into said mixture ($M_2$), while maintaining the pH at a value greater than or equal to 9 by the joint addition of sodium hydroxide or potassium hydroxide, said step e) resulting in the formation of a mixture ($M_3$);

a step e) during which said mixture ($M_3$) is acidified until a pH of less than or equal to 3 is reached;

a step f) of decantation for the purpose of drawing off the mother liquors;

at least one step g) of washing with brined water to obtain, after decantation, said desired composition.

9. A method for preparing a cosmetic, dermocosmetic, dermopharmaceutical or pharmaceutical composition for topical use (C) comprising a mass proportion of greater than or equal to 5% by mass and less than or equal to 30% by mass of a compound of formula (I') or of a mixture of compounds of formula (I'):

X—[CH$_2$]$_p$—C(=O)—Y—O$^-$M$^+$ (I'), in which X represents a methyl radical, p represents an integer greater than or equal to 10 and less than or equal to 20, M$^+$ represents a sodium cation, Y represents either a divalent radical of formula (II$_a$):

—[N(R$_3$)—CH(R$_2$)—C(=O)—]$_m$— (II$_a$), in which $R_3$ represents a hydrogen atom or a methyl radical, m represents an integer greater than or equal to 1 and less than or equal to 4 and $R_2$ represents a hydrogen atom or a radical chosen from methyl, isopropyl, isobutyl, 1-methylpropyl, benzyl and 3-aminopropyl radicals, or a divalent radical of formula ($II_b$):

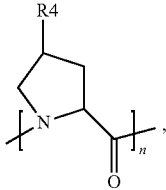

in which $R_4$ represents a hydrogen atom or a hydroxyl radical and n represents an integer greater than or equal to 1 and less than or equal to 4; and X represents either a methyl radical or a monovalent radical of formula (III):

$$HO-Y'-C(=O)- \quad (III),$$

in which Y' represents either the divalent radical of formula ($II_a$) as defined previously, or the divalent radical of formula (IIb) as defined previously, it being understood that when X represents the radical of formula (III), Y and Y' are identical;

(b) —A mass proportion of greater than 5% by mass and less than or equal to 30% by mass of a linear or branched alkanediol containing from six to eight carbon atoms;

(d) —a mass proportion of greater than 40% by mass and less than 90% by mass of water, it being understood that the pH of said composition (C) is less than or equal to 9 and greater than or equal to 5.5, said method comprising a step h), during which the necessary quantities of linear or branched alkanediol containing from six to eight carbon atoms, of aqueous sodium hydroxide solution and of water are added simultaneously or sequentially to the composition ($C_1$) as defined in claim 1 to obtain the proportions and pH value as defined above.

10. A method for preparing the composition ($C_1$) as defined in claim 1, comprising the following successive steps:

—a step a) during which said alkanediol containing from six to eight carbon atoms is mixed with water to form a mixture ($S_1$) containing, per 100% of mass, from 5% by mass to 70% by mass of said alkanediol and from 30% by mass to 95% by mass of water;

a step b) during which a compound of formula ($VI_a$):

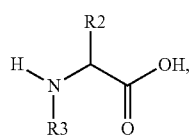

or of formula ($IV_b$):

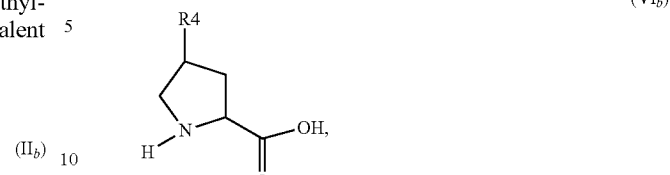

or a mixture of at least one compound of formula ($VI_a$) or ($VI_b$) with at least one other compound of formula ($VI_a$) or ($VI_b$) is added to said mixture ($S_1$) in a proportion such that the mixture ($M_1$) obtained contains, per 100% of its mass, from 5% by mass to 50% by mass of said compound of formula ($VI_a$) or ($VI_b$) or of said mixture of compounds of formula ($VI_a$) and/or ($VI_b$) and from 50% by mass to 95% by mass of said mixture ($S_1$);

a step c) during which sodium hydroxide or potassium hydroxide is added to said mixture ($M_1$) to form a mixture ($M_2$) having a pH greater than or equal to 9;

a step d) during which an acid chloride of formula (VII):

$$X-[CH_2]_p-C(=O)-Cl \quad (VII),$$

in which X and p are as defined in formula (I) above, or a mixture of acid chlorides of formula (VII), is poured into said mixture ($M_2$), while maintaining the pH at a value greater than or equal to 9 by the joint addition of sodium hydroxide or potassium hydroxide, said step e) resulting in the formation of a mixture ($M_3$);

a step e) during which said mixture ($M_3$) is acidified until a pH of less than or equal to 3 is reached; and a step f) of decantation for the purpose of drawing off the mother liquors.

11. The composition ($C_1$) as defined in claim 2, wherein in formulae (I) and (V), the monovalent radical $X-(CH_2)_p-C(=O)-$ represents the palmitoyl radical.

12. The composition ($C_1$) as defined in claim 3, wherein in formulae (I) and (V), the monovalent radical $X-(CH_2)_p-C(=O)-$ represents the palmitoyl radical.

13. The composition ($C_1$) as defined in claim 4, wherein in formulae (I) and (V), the monovalent radical $X-(CH_2)_p-C(=O)-$ represents the palmitoyl radical.

14. The composition ($C_1$) as defined in claim 5, wherein in formulae (I) and (V), the monovalent radical $X-(CH_2)_p-C(=O)-$ represents the palmitoyl radical.

15. The composition ($C_1$) as defined in claim 2, wherein said diol containing from six to eight carbon atoms is chosen from 1,6-hexanediol, 1,2-hexanediol, 2-methyl 2,4-pentanediol or 1,2-octanediol.

16. The composition ($C_1$) as defined in claim 3, wherein said diol containing from six to eight carbon atoms is chosen from 1,6-hexanediol, 1,2-hexanediol, 2-methyl 2,4-pentanediol or 1,2-octanediol.

17. The composition ($C_1$) as defined in claim 4, wherein said diol containing from six to eight carbon atoms is chosen from 1,6-hexanediol, 1,2-hexanediol, 2-methyl 2,4-pentanediol or 1,2-octanediol.

18. The composition ($C_1$) as defined in claim 5, wherein said diol containing from six to eight carbon atoms is chosen from 1,6-hexanediol, 1,2-hexanediol, 2-methyl 2,4-pentanediol or 1,2-octanediol.

19. The composition ($C_1$) as defined in claim 6, wherein said diol containing from six to eight carbon atoms is chosen from
1,6-hexanediol, 1,2-hexanediol, 2-methyl 2,4-pentanediol or 1,2-octanediol.

20. A method for preparing the composition ($C_1$) as defined in claim 2, comprising the following successive steps:
a step a) during which said alkanediol containing from six to eight carbon atoms is mixed with water to form a mixture ($S_1$) containing, per 100% of mass, from 5% by mass to 70% by mass of said alkanediol and from 30% by mass to 95% by mass of water;
a step b) during which a compound of formula ($VI_a$):

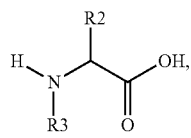

(VI$_a$)

or of formula ($IV_b$):

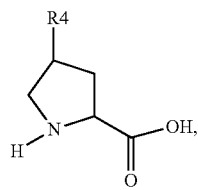

(VI$_b$)

or a mixture of at least one compound of formula ($VI_a$) or ($VI_b$) with at least one other compound of formula ($VI_a$) or ($VI_b$) is added to said mixture ($S_1$) in a proportion such that the mixture ($M_1$) obtained contains, per 100% of mass, from 5% by mass to 50% by mass of said compound of formula ($VI_a$) or ($VI_b$) or of said mixture of compounds of formula ($VI_a$) and/or ($VI_b$) and from 50% by mass to 95% by mass of said mixture ($S_1$);

a step c) during which sodium hydroxide or potassium hydroxide is added to said mixture ($M_1$) to form a mixture ($M_2$) having a pH greater than or equal to 9;

a step d) during which an acid chloride of formula (VII):

$$X—[CH_2]_p—C(=O)—Cl \qquad (VII),$$

in which X and p are as defined in formula (I) above, or a mixture of acid chlorides of formula (VII), is poured into said mixture ($M_2$), while maintaining the pH at a value greater than or equal to 9 by the joint addition of sodium hydroxide or potassium hydroxide, said step e) resulting in the formation of a mixture ($M_3$);

a step e) during which said mixture ($M_3$) is acidified until a pH of less than or equal to 3 is reached;

a step f) of decantation for the purpose of drawing off the mother liquors;

at least one step g) of washing with brined water to obtain, after decantation, said desired composition.

* * * * *